United States Patent [19]
Faupel et al.

[11] Patent Number: 5,660,177
[45] Date of Patent: Aug. 26, 1997

[54] D.C. BIOPOTENTIAL SENSING ELECTRODE ASSEMBLIES FOR APPARATUS FOR DISEASE, INJURY AND BODILY CONDITION SCREENING OR SENSING

[75] Inventors: Mark L. Faupel, Conyers; Burke T. Barrett, Roswell; John D. Stephens; Seth D. Nathanson, both of Alpharetta, all of Ga.

[73] Assignee: Biofield Corp., Roswell, Ga.

[21] Appl. No.: 325,085

[22] Filed: Oct. 17, 1994

Related U.S. Application Data

[63] Continuation-in-part of Ser. No. 27,539, Mar. 8, 1993, Pat. No. 5,415,164, which is a continuation-in-part of Ser. No. 787,641, Nov. 4, 1991, Pat. No. 5,217,014.

[51] Int. Cl.⁶ ................................................ A61B 5/04
[52] U.S. Cl. .................................... 128/639; 128/640
[58] Field of Search ................................ 128/639, 640, 128/641, 653.1, 644, 696; 606/12

[56] References Cited

U.S. PATENT DOCUMENTS

| | | |
|---|---|---|
| Re. 31,454 | 12/1983 | Hymes . |
| 3,027,333 | 3/1962 | Friedman . |
| 3,567,657 | 3/1971 | Lichtenstein . |
| 3,828,766 | 8/1974 | Krasnow . |
| 3,868,946 | 3/1975 | Hurley . |
| 3,964,469 | 6/1976 | Manley . |
| 3,976,055 | 8/1976 | Monter et al. . |
| 3,989,035 | 11/1976 | Zuehlsdorff . |
| 4,034,854 | 7/1977 | Bevilacqua . |
| 4,114,263 | 9/1978 | Szpur . |
| 4,126,126 | 11/1978 | Bare et al. . |
| 4,166,453 | 9/1979 | McClelland . |
| 4,282,878 | 8/1981 | Novello . |
| 4,311,152 | 1/1982 | Modes et al. ............... 128/641 |
| 4,317,278 | 3/1982 | Carmon et al. . |
| 4,362,165 | 12/1982 | Carmon et al. . |
| 4,365,634 | 12/1982 | Bare et al. . |
| 4,441,500 | 4/1984 | Sessions et al. ............. 128/641 |
| 4,570,637 | 2/1986 | Gomes et al. . |
| 4,580,557 | 4/1986 | Hertzmann ..................... 606/12 |
| 4,583,549 | 4/1986 | Manoli . |
| 4,617,935 | 10/1986 | Cartmell et al. ............. 128/641 |
| 4,742,828 | 5/1988 | Sundstrom . |
| 4,763,660 | 8/1988 | Kroll et al. . |
| 4,787,390 | 11/1988 | Takata . |
| 4,955,383 | 9/1990 | Faupel ......................... 128/639 |
| 4,957,109 | 9/1990 | Groeger et al. . |
| 5,042,481 | 8/1991 | Suzuki et al. . |
| 5,499,628 | 3/1996 | Wright ......................... 128/641 |

*Primary Examiner*—Lee S. Cohen
*Attorney, Agent, or Firm*—Sixbey, Friedman, Leedom & Ferguson

[57] ABSTRACT

A DC biopotential sensing electrode assembly is provided for an apparatus for sensing DC biopotentials present at the skin of a subject. The electrodes include an electroconductive medium for transmitting ions from the skin which has a chloride content within a range of from 6–15 grams per hundred grams of such medium. To reduce the corrosive effect of this electroconductive medium, each electrode includes only one metallic component, and to provide an electrode with a low AC impedance, this metal is uniformly coated upon nonmetallic sensor and terminal bodies with a coating thickness within a range of from 0.5 to 1.5 mil. To insure a complete electrical path through both the sensor and the terminal bodies, the nonmetallic portions are formed of conductive plastic.

27 Claims, 6 Drawing Sheets

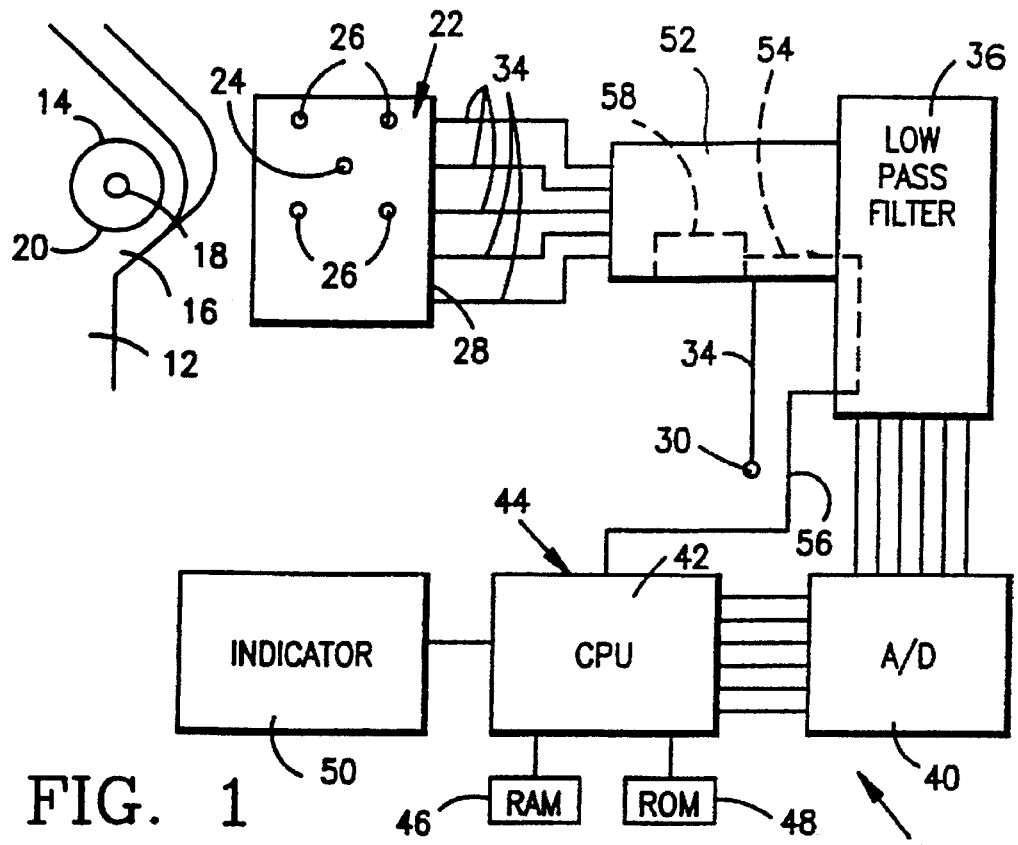
FIG. 1
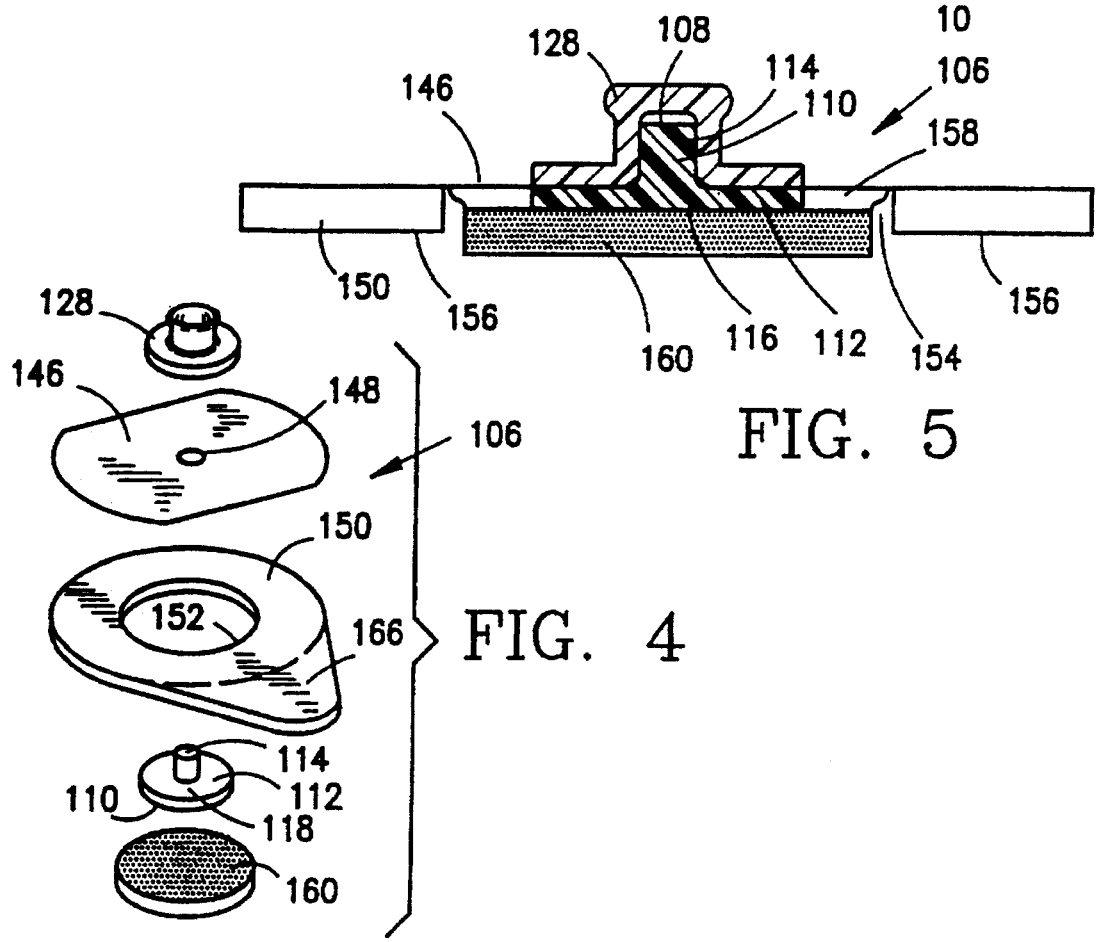
FIG. 5
FIG. 4

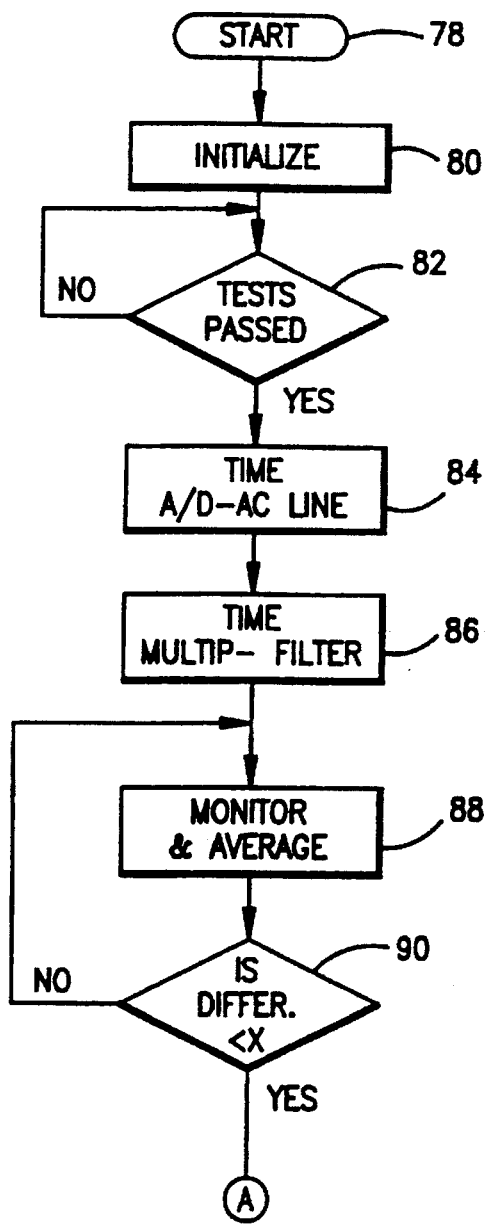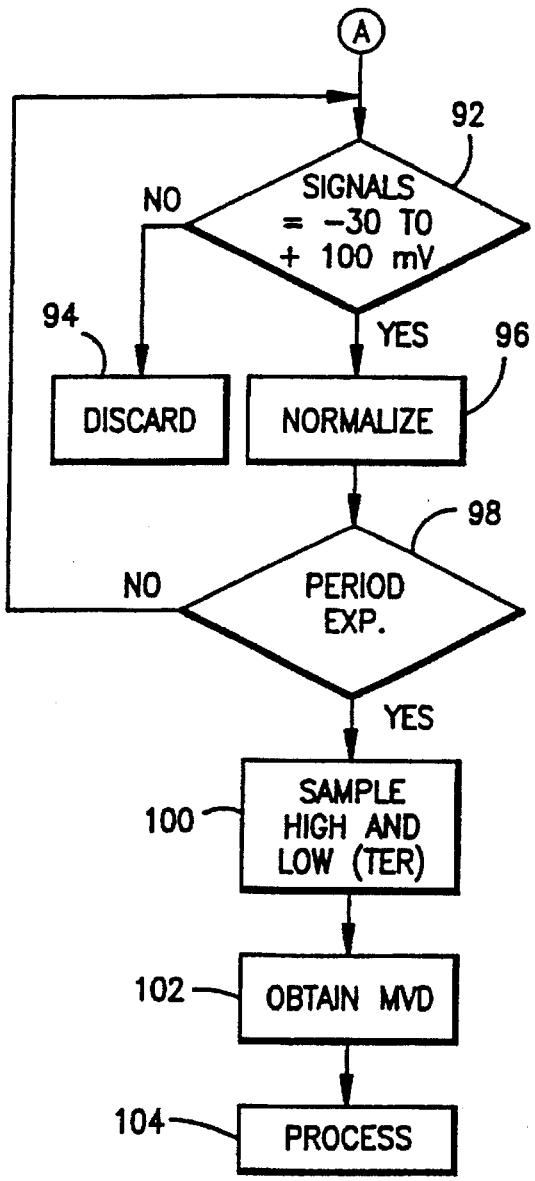
FIG. 2
FIG. 3

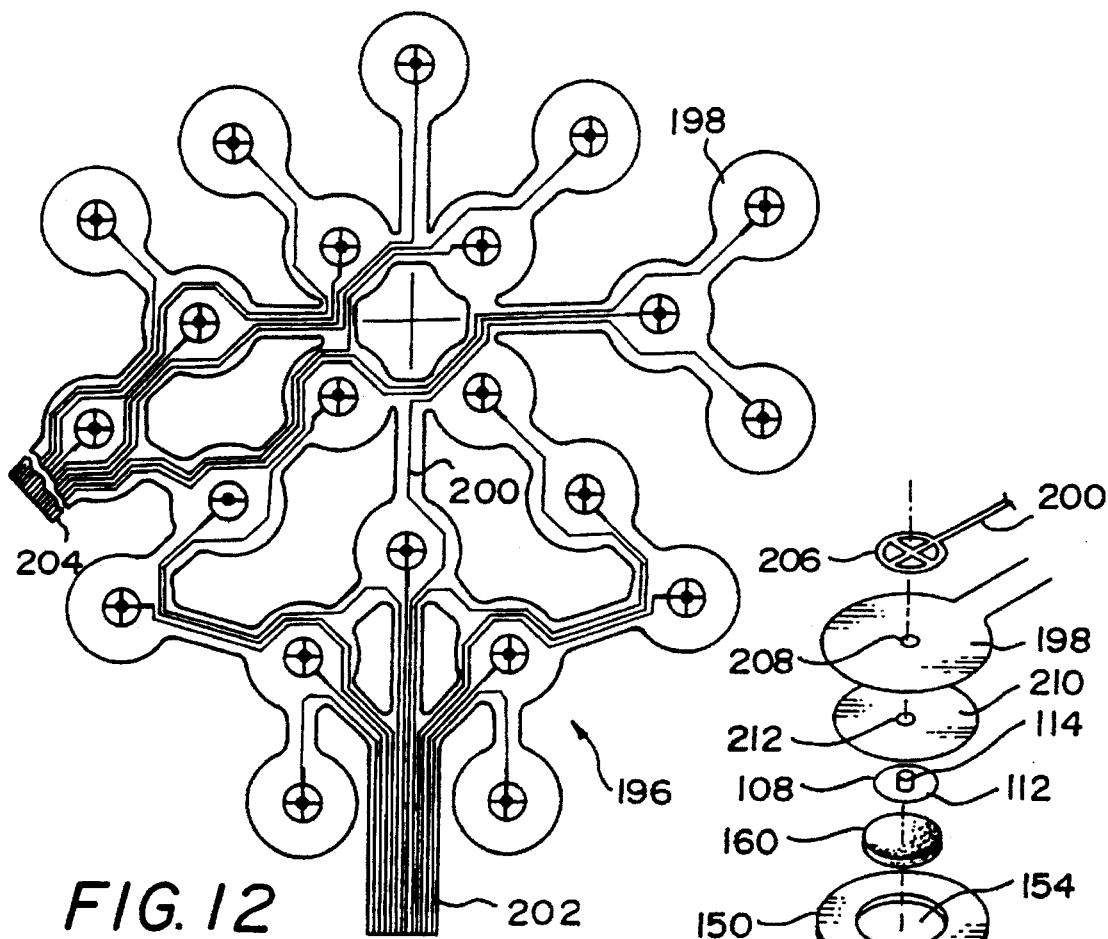
FIG. 12
FIG. 13
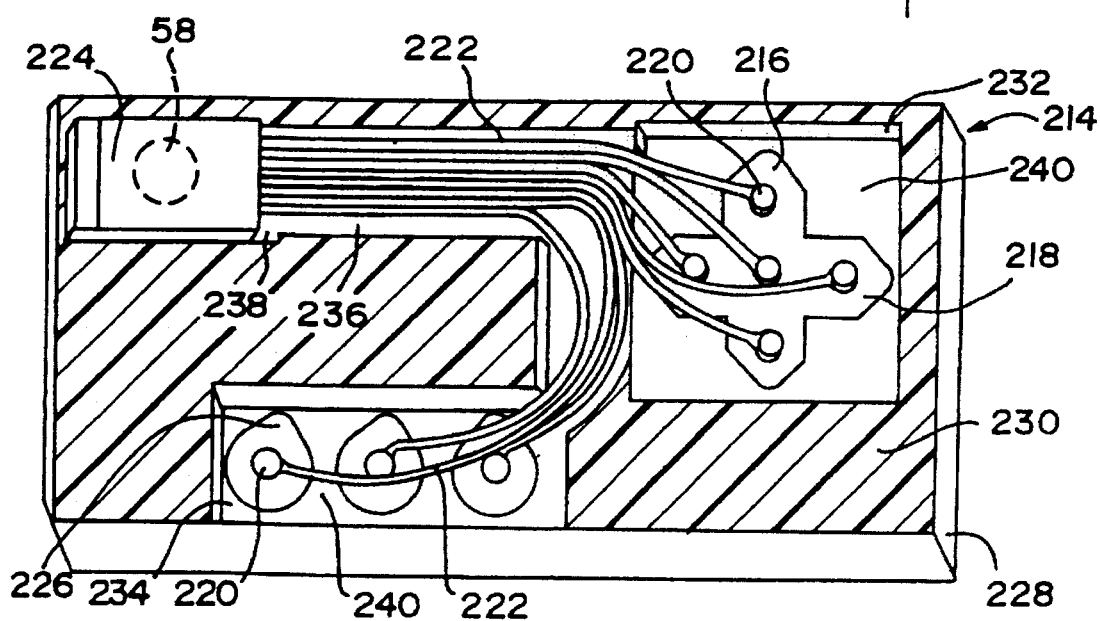
FIG. 14

D.C. BIOPOTENTIAL SENSING ELECTRODE ASSEMBLIES FOR APPARATUS FOR DISEASE, INJURY AND BODILY CONDITION SCREENING OR SENSING

This application is a continuation-in-part application of Ser. No. 08/027,539 filed Mar. 8, 1993, now U.S. Pat. No. 5,415,164, which is a continuation-in-part application of Ser. No. 787,641 filed Nov. 4, 1991, now U.S. Pat. No. 5,217,014.

TECHNICAL FIELD

The present invention relates generally to an apparatus for screening or sensing disease states, injury sites or bodily conditions in a living organism by detecting the DC biopotential of the electromagnetic field present between a reference and a plurality of test points on the living organism to measure the gradient of electrical activity which occurs as a function of biological activity, and more particularly to DC biopotential sensing electrode assemblies for use with such apparatus.

BACKGROUND ART

In recent years the theory that measurement of the potential level of the electromagnetic field of a living organism can be used as an accurate screening and diagnostic tool is gaining greater acceptance. Many methods and devices have been developed in an attempt to implement this theory. For example, U.S. Pat. No. 4,328,809 to B. H. Hirschowitz et al. deals with a device and method for detecting the potential level of the electromagnetic field present between a reference point and a test point on a living organism. Here, a reference electrode and a test electrode provide DC signals indicative of the potential level of the electromagnetic field measured between the reference point and the test point. These signals are provided to an analog-to-digital converter which generates a digital signal as a function thereof, and a processor provides an output signal indicative of a parameter or parameters of the living organism as a function of this digital signal.

Similar biopotential measuring devices are shown by U.S. Pat. Nos. 4,407,300 to Davis, and 4,557,271 and 4,557,273 to Stroller et al. Davis, in particular, discloses the diagnosis of cancer by measuring the electromotive forces generated between two electrodes applied to a subject.

Often, the measurement of biopotentials has been accomplished using an electrode array, with some type of multiplexing system to switch between electrodes in the array. The aforementioned Hirschowitz et al. patent contemplates the use of a plurality of test electrodes, while U.S. Pat. Nos. 4,416,288 to Freeman and 4,486,835 to Bai disclose the use of measuring electrode arrays.

Unfortunately, previous methods for employing biopotentials measured at the surface of a living organism as a diagnostic tool, while basically valid, are predicated upon an overly simplistic hypothesis which does not provide an effective diagnosis for many disease states. Prior methods and devices which implement them operate on the basis that a disease state is indicated by a negative polarity which occurs relative to a reference voltage obtained from another site on the body of a patient, while normal or non-malignant states, in the case of cancer, are indicated by a positive polarity. Based upon this hypothesis, it follows that the detection and diagnosis of disease states can be accomplished by using one measuring electrode situated externally on or near the disease site to provide a measurement of the polarity of the signal received from the site relative to that from the reference site. Where multiple measuring electrodes have been used, their outputs have merely been summed and averaged to obtain one average signal from which a polarity determination is made. This approach can be subject to major deficiencies which lead to diagnostic inaccuracy, particularly where only surface measurements are taken.

First, the polarity of diseased tissue underlying a recording electrode has been found to change over time. This fact results in a potential change which confounds reliable diagnosis when only one external recording electrode is used. Additionally, the polarity of tissue as measured by skin surface recording is dependent not only upon the placement of the recording electrode, but also upon the placement of the reference electrode. Therefore, a measured negative polarity is not necessarily indicative of diseases such as cancer, since polarity at the disease site depends in part on the placement of the reference electrode.

As disease states such as cancer progress, they produce local effects which include changes in vascularization, water content, and cell division rate. These effects alter ionic concentrations which can be measured at the skin surface and within the neoplastic tissues. Other local effects, such as distortions in biologically closed electrical circuits, may occur. A key point to recognize is that these effects do not occur uniformly around the disease site. For example, as a tumor grows and differentiates, it may show wide variations in its vascularity, water content and cell division rate, depending on whether examination occurs at the core of the tumor (which may be necrotic) or at the margins of the tumor (which may contain the most metabolically active cells). The tumor may not respond significantly to growth factors, while the growth factors and the enzymes produced may significantly affect the normal cells surrounding the tumor. Once this fact is recognized, it follows that important electrical indications of disease are going to be seen in the relative voltages recorded from a number of sites at and near a diseased area, and not, as previously assumed, on the direction (positive vs. negative) of polarity.

The accurate measurement of DC biopotentials for sensing or screening for disease, injury or bodily functions is very difficult to accomplish, for the DC potentials to be sensed are of a very low amplitude. Due to factors such as the low DC potentials involved and the innate complexity of biological systems, the collected data signals tend to include a substantial volume of noise which makes accurate analysis difficult. Also, biological systems are notorious for their complexity, nonlinearity and nonpredictability, and wide variations from the norm are not uncommon. For example, DC biopotential signals tend to drift over time, so that if signals are not sensed and analyzed with some rapidity, signal errors due to drift occur.

For the accurate measurement of DC biopotentials for disease diagnosis and screening, electrode and electrode circuit characteristics and electrode placement become important. Factors such as small DC offset potentials in the low millivolt range, which may have little effect on an AC biopotential measurement, such as ECG measurement, can destroy the accuracy of a DC biopotential measurement. For screening applications where many sensing electrodes are used, it is often critical for electrode characteristics to be uniform, for accurate electrode spacing to be maintained and for DC offsets to be substantially eliminated.

Many DC biopotential sensing electrodes are packaged in a pre-gelled state wherein an electrolytic paste or gel is packaged as part of the electrode. The gel may be located in a central gell reservoir consisting of a molded cup, or it may be contained in a dye-cut hole in a foam which encapsulates a gel saturated open cell compressible foam column. In most instances, the pre-gelled electrodes are sold ready for use with an electrically conductive material such as metal or a metal chloride in contact with the electrolyte gel.

A pre-gelled electrode system is generally not a battery by itself, but forms a part of a battery-system consisting of two or more electrodes placed on the body. In such a system, a complex battery is formed consisting of many interactive components including the electrode material (frequently silver/silver chloride), the electrode gel, internal body chemistry and external skin conditions, skin preparation, temperature, air condition and chemistry, etc. Obviously, some of these factors are not subject to control, but in order to get the best data possible, especially in instances where DC biopotentials are of interest, artifacts, such as DC offsets, should be reduced to the lowest level. Most pre-gelled electrodes when introduced in the battery system outlined above contribute some unwanted DC voltage (polarization effect) to biopotential measurements. It is important to lower the possibility of such DC artifacts occurring to a degree sufficient to preclude them from having a substantial adverse effect on biopotential measurements.

The design and performance characteristics for an effective DC biopotential electrode are different from those of electrodes designed for measuring alternating current (AC) signals such as those used with electrocardiology (ECG) and electroencephalography (EEG). For example, U.S. national standards for single use ECG electrodes allow the DC offset of an electrode pair (i.e., fie spurious DC current generated by electrochemical interactions between electrode components) to be as high as 100 millivolts (ANSI/AAMI standard). Since effective use of DC signals for cancer diagnosis requires discrimination at the one millivolt level, standards for ECG electrodes are grossly excessive. ECG electrodes are intended for AC measurements which are not significantly affected by DC offset voltages in the electrode to the degree that DC biopotential measurements are adversely affected by such offset voltages. The traditional view taken in the manufacture of ECG pregelled electrodes is that to reduce DC offset, one must sacrifice AC impedance, and since a low AC impedance is most important in an ECG pregelled electrode, the DC offset voltage is tolerated. However, for highly accurate DC biopotential measurements, both the DC offset potential and the AC impedance for the electrode must be low.

When DC biopotential measurements are taken from the skin of a subject with conventional EGG electrodes, sweat gland activity creates noise which tends to mask the sensed DC signal, and the provision of an electrode structure to minimize this noise is essential.

If a pre-gelled electrode array is to be used effectively for disease detection, such as breast cancer screening, the array will require a relatively large number of spaced electrodes to cover substantially the entire surface of the breast. Not only must each of these electrodes be free from error causing offset potentials before use, but the electrodes must maintain contact with the curved surface of the breast without movement during the screening procedure and must maintain a predetermined array formation with specified electrode spacing. Consistent location and orientation of the electrical channels connected to the respective electrodes must also be maintained to prevent incorrect connection to the electrodes and to maintain positive contact between the electrodes and the electrical channel leads therefor.

In the past, these objectives have not been met with an apparatus which could be rapidly applied and worn comfortably by a patient, and which also produces reliable DC measurements.

The key to effective measurement and analysis of direct current skin potentials is absolute maintenance of signal integrity from the skin surface to the signal processing components of the measuring unit. This is especially critical due to the inherent low amplitude of biologic DC potentials. At any point in the electronic path from the skin sensing electrode to the measuring unit, potential exists for noise to intrude upon signal, thereby degrading diagnostically useful information.

DISCLOSURE OF THE INVENTION

It is a primary object of the present invention to provide a novel and improved biopotential sensing electrode having a low DC offset and a low AC impedance.

Another object of the present invention is to provide a novel and improved DC biopotential sensing electrode which includes a gel or cream for transmitting ions from the skin of a subject to an electrode sensing element wherein the gel or cream includes a chloride content which is within the range of chloride that is an isotonic or hypertonic fluids.

A further object of the present invention is to provide a novel and improved DC biopotential sensing electrode having dual conductive paths through the electrical conductive elements of the electrode.

Yet another object of the present invention is to provide a novel and improved DC biopotential sensing electrode formed with a gel or cream having a high chloride ion content and an electrode structure which is resistant to corrosion caused by ions in the gel or cream.

Another object of the present invention is to provide a novel and improved electrode and cable assembly which terminates at a single connector which may be connected to a connector for a cable system leading to a processor unit. The connector includes means to transmit identification signals to the processor unit.

A further object of the present invention to provide a novel and improved electrode positioning harness for use with a biopotential measuring electrode array and device for disease, injury and bodily condition screening and sensing.

A still further object of the present invention is to provide a novel and improved electrode positioning harness for use with a biopotential measuring electrode array for breast cancer screening which will effectively and comfortably accommodate various breast sizes based upon anthropometric data.

BRIEF DESCRIPTION OF THE DRAWINGS

FIG. 1 is a block diagram of the apparatus for disease, injury and bodily condition screening or sensing with the DC biopotential sensing electrode assembly of the present invention;

FIG. 2 is a flow diagram illustrating the operation of the apparatus of FIG. 1;

FIG. 3 is a flow diagram illustrating the operation of the apparatus of FIG. 1;

FIG. 4 is an exploded view of a DC biopotential sensing electrode for use with the apparatus of FIG. 1;

FIG. 5 is a cross sectional view of the electrode of FIG. 4;

FIG. 12 is a plan view of a second embodiment of a lattice electrode array of the present invention;

FIG. 13 is an exploded view of an electrode structure and pad of the lattice electrode array of FIG. 12; and FIG. 14 is a perspective top view of a third embodiment of an electrode array of the present invention and the packaging therefor.

BEST MODE FOR CARRYING OUT THE INVENTION

Figure 6:
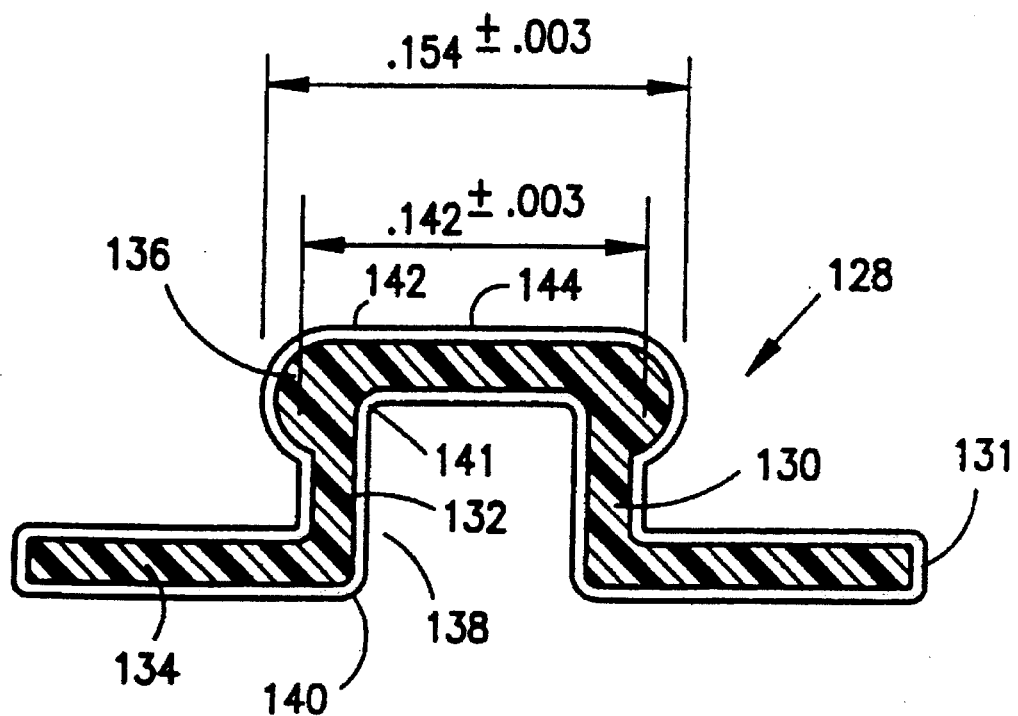
FIG. 6 is a cross sectional view of the terminal for the electrode of FIG. 4.
Figure 7:
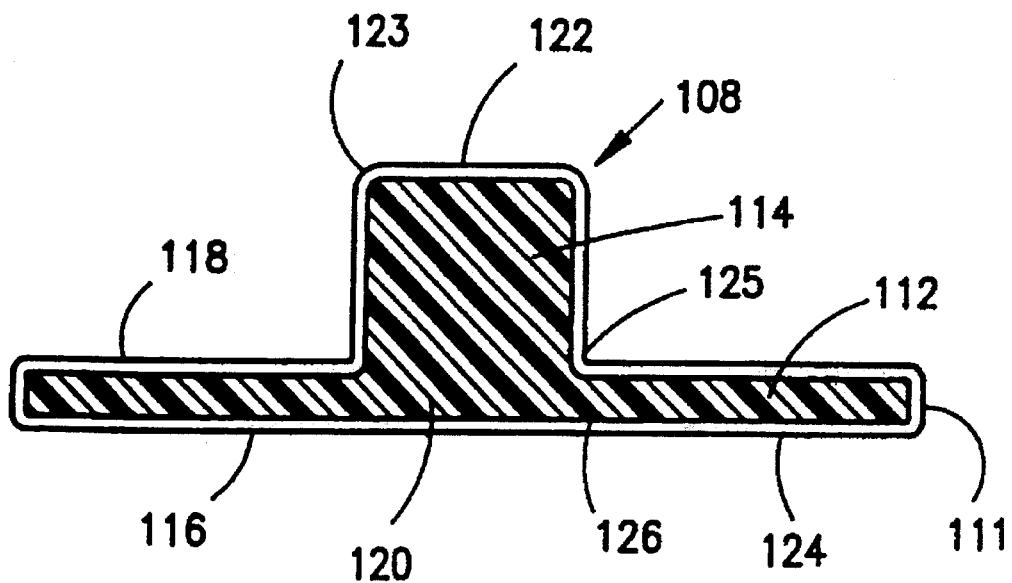
FIG. 7 is a cross sectional view of the sensor for the electrode of FIG. 4.

FIG. 1 discloses a basic block diagram of the measuring apparatus 10 for performing an analysis for indicating the presence, absence or state of a condition at a test site on a human or animal subject. For purposes of illustration, the apparatus 10 will be described in connection with methods involving the screening or sensing of breast cancer. However, it should be recognized that the apparatus can be similarly employed for providing an indication of disease, injury or other body condition of a living human or animal.

In FIG. 1, a human subject 12 may have a cancerous lesion 14 on one breast 16. This cancerous lesion has a core 18 and an outer zone 20 surrounding the core where various differing local effects, such as changes in vascularization, water content and cell division rate occur. Assuming first, for purposes of discussion, that the location of the lesion 14 is now known, and the device 10 is to be used to screen the breast 16 to determine whether or not a disease condition exists, skin surface potentials will be measured in an area of the breast, including the zone 20 using an electrode array 22. In FIG. 1, the electrode array includes a central electrode 24 surrounded by four peripheral electrodes 26, all of which are skin surface electrodes. However, this invention contemplates the use of a variety of different electrode arrays depending upon the intended application for which the device 10 is used. For example, in the diagnosis of clinically symptomatic breast or skin lesions, the electrode array should cover various areas of the lesion as well as relatively normal tissue near the lesion site. For breast cancer screening (where patients are asymptomatic), the array should give maximum coverage of the entire breast surface. The aim in both of these areas is to measure the gradient of electrical activity which occurs as a function of the underlying biological activity of the organ system. The number of electrodes used in the measurement will also be a function of specific application, and breast cancer screening may require the use of as few as twelve or as many as sixty or more electrodes for each breast, while in screening for prostate cancer, as few as two measurement electrodes might be used.

The core electrode 24 and the peripheral electrodes 26 are mounted upon a flexible backing sheet 28 which permits the electrodes to be positioned against the curved surface of the breast 16 while still maintaining the position of the electrodes in predetermined pattern. However, other electrode arrays may be employed wherein each individual electrode can be individually positioned, and the relative position between electrodes can be altered. The electrode array 22 is used in conjunction with one or more reference skin surface electrodes 30, and all of these electrodes are of a type used for detecting the potential level of the DC electromagnetic field present in a living organism.

The device 10 is shown as a multi-channel device having electrode leads 34 extending separately from the central electrode 24, the peripheral electrodes 26, and the reference electrode 30 to a low pass filter amplifier 36. This filter amplifier operates to remove some undesirable high frequency AC components which appear on the slowly varying DC voltage signal outputs provided by each of the electrodes as a result of the electromagnetic field measurement.

The output from the filter amplifier 36 is provided to an analog-to-digital converter 40 which converts each analog signal received thereby to a digital signal to be provided to the input of a central processing unit (CPU) 42. Of course, for some applications, the central processing unit may respond directly to analog input signals or to digital or other coded signals produced directly by the electrode array 22, and in such cases, the analog to digital converter 40 and possibly even the filter 36 would be eliminated and the output from the electrode array would input directly to the CPU. The central processing unit is a component of a central control unit indicated generally at 44 which includes RAM and ROM memories 46 and 48. Digital input data from the analog-to-digital converter 40 is stored in memory and is processed by the CPU 42 in accordance with a stored program to perform various pattern recognition methods to be described. The digital signals may be subjected to digital filtering by the CPU before processing. The information derived by the CPU as a result of this processing is then fed to a suitable indicator device 50 which may constitute a printer, a CRT display device, a storage tape or disc, or a combination of such conventional indicators.

It is important that no biopotential measurements be taken using the device 10 if an array containing electrodes designed for sensing DC biopotentials is not connected to provide the electrode array 22 and the reference electrode 30. One structure for accomplishing this incorporates the leads 34 into a cable 52 which is used to removably connect the electrode array 22 and the reference electrode 30 to the low pass filter amplifier 36. This cable can be a multichannel cable or a single channel cable, depending upon whether or not electrode multiplexing is employed. A conventional connector, not shown, is provided to connect one end of the cable to the low pass filter 36, or with a single channel filter, the connector may be plugged to a sequencing switch. Each cable lead 34 is connected to the output terminal for one of the electrodes in the electrode array 22.

When the cable 52 is connected to the low pass filter amplifier 36, a separate connection is made between a conductor 54 within the cable and a conductor 56 leading directly to the CPU 42. The conductor 54 leads to an address identification chip 58 of known type which responds to an address interrogation signal provided over the conductor 54 to the address chip. The proper address interrogation signal is stored in the memory for the central control unit 44 and is sent over the conductor 56 by the CPU 42 when the apparatus 10 is initially activated. If this interrogation signal corresponds to a signal to which the address chip 58 responds, then a response from the address chip is passed by the conductors 54 and 56 back to the CPU 42 and the CPU initiates a measurement operation in response to a control program stored in the memory for the central control unit. Alternatively, if the wrong address chip, no address chip or no electrode array connection is present, no response is received from the address interrogation signal and the CPU 42 does not proceed with the stored control program.

In addition to the address chip 58, the central control unit 44 can be made responsive to other parameters in the electrode array 22 during an initial test period to assure that an acceptable electrode array is in place before a measurement program is begun. As has been previously indicated, the presence of an offset potential in the electrode array is detrimental to the accuracy of DC biopotential measurements, and the magnitude of this offset potential can be measured during the test period of the apparatus 10. If the measured offset potential is less than a predetermined level, then the CPU may continue with a measurement operation in response to the stored control program, but if the offset potential exceeds the predetermined level, the measurement operation is not initiated by the CPU.

The electrodes which are used as the electrodes 24, 26 and 30 should be manufactured to specific electrical tolerances if they are to be effectively used to provide accurate DC biopotential measurements. The electrical characteristics of each electrode are determined by elements of construction such as electrode size, the type of gel or cream used, and the types of metals and other materials used in constructing the electrode. These electrical characteristics may be measured in the same manner as the offset potential, and the measurement operation can be cancelled by the CPU if the proper electrode characteristics are not present.

It is important to recognize that the CPU 42 can be programmed to run identification tests on a variety of electrode combinations, since diverse DC biopotential measurement applications require the use of different numbers of electrodes. Thus, the electrical characteristics of as few as two electrodes, a reference and a measurement electrode, plus a plurality of acceptable electrode array combinations would be stored in the memory of the control unit 44. It is also possible to provide each individual electrode with an address identification chip 58 having a lead or terminal 56 which could plug into a test block connected to the CPU. This would permit each individual electrode to be used during a measurement operation to be identified by the CPU 42 during an initialization operation.

Although the unit 58 has been identified as an address identification chip, this unit constitutes any structure which responds to an interrogation signal in a definable manner. For example, the unit 58 could be formed by a particular material having a specific response characteristic to an interrogation signal, and this material could actually be one which is used in the construction of the individual electrodes.

The operation of the apparatus 10 will be clearly understood from a brief consideration of the broad method steps of the invention which the device is intended to perform. The electrode array 22 is positioned with electrodes 24 and 26 located over various diverse areas of a test site, and the reference electrode 30 is then brought into contact with the skin of the subject in spaced relationship to the electrode arrays. This reference electrode might, for example, be brought into contact with a hand of the subject. The electromagnetic field between the reference electrode and each of the electrodes 24 and 26 is measured, converted to a digital signal and stored for processing by the control unit 44. The program control for the central processor unit 42 causes a plurality of these measurements to be taken over a period of time, and the measurements on all channels are taken repetitively during a predetermined measurement time or test period. Sequential measurements between the reference electrode and one of the electrodes in the array 22 are taken until each channel is sampled, and then the sequential measurement is repeated throughout the duration of the predetermined test period. In prior art units, a plurality of measurements have been taken over a period of time and often from a plurality of electrodes, but then these plural measurements are merely averaged to provide a single average output indication. In accordance with the method of the present invention, the measurement indications on each individual channel are not averaged with those from other channels, but are instead kept separate and averaged by channel within the CPU 42 at the end of the test period. For the duration of a single test period, for example, for the five measurement channels shown, the CPU will obtain five average signals indicative of the average electromagnetic field for the test period between the reference electrode 30 and each of the electrodes 24 and 26 in the electrode array 22. Of course, more reference electrodes can be used, although only one reference electrode has been shown for purposes of illustration.

Having once obtained an average signal level indication for each channel, the results of the measurements taken at multiple sites are analyzed in terms of a mathematical analysis to determine the relationships between the average signal values obtained. It has been found that the result of such an analysis is that a subset of relationships can be obtained which are indicative of the presence of more serious disease, injury or other condition, while a different subset might be obtained which will be indicative of the absence of such conditions.

One important relationship to be obtained is designated the maximum voltage differential (MVD), which is defined as the minimum average voltage value obtained during the test period subtracted from the maximum average voltage value obtained for the same period where two or more electrodes are recording DC potentials from a test site relative to the same reference. Thus, for each predetermined test period, the lowest average voltage level indication obtained on any of the channels is subtracted from the highest average voltage level indication obtained on any of the channels to obtain an MVD voltage level. If this MVD voltage level is above a desired level <x, then a disease condition, such as a malignancy, injury or other condition could be indicated. Similarly, if the average taken over the measurement period from one channel is an abnormally low value <y, the presence of this abnormally low individual electrode reading (IER) could be indicative of a disease condition, injury or other condition. These primary indicators may be further analyzed to reduce the number of false positive diagnosis which may be falsely identified on the basis of high MVD or low IER readings.

The general overall operation of the central processing unit 42 will best be understood with reference to the flow diagrams of FIGS. 2 and 3. The operation of the unit 10 is started by a suitable start switch as indicated at 78 to energize the central processing unit 42, and this triggers an initiate state 80. In the initiate state, the various components of the device 10 are automatically brought to an operating mode, with for example, the indicator 50 being activated while various control registers for the central processing unit are reset to a desired state.

Subsequently, a test period is initiated at 82 wherein the various components of the system are tested for proper operability. During this test period, the electrode array 22 may also be tested to make certain that electrodes are being used which accurately measure DC biopotentials. This would involve interrogation of the address chip 58 and possibly the testing for other electrode characteristics. The address chip may be included in a disposable cable connector to be subsequently described, and it can be important that this cable connector be adapted for only one use. Therefore, the central processing unit may have the ability to disable the address chip once a proper address is received so that the cable connector cannot be reused with improper electrodes to provide a new address signal. This can be accomplished in a number of ways. For example, the address chip 58 may be an EE PROM containing the address combined with a signal activated erase circuit for the EE PROM. Once the central processor receives the proper address, it would send a command signal to the erase circuit to erase the EE PROM.

Another simple deactivation circuit would include a small fuse unit in the line 54 portion of a cable connector. Once the central processor receives the proper address, it would send a command signal over the line 56 to burn out or blow the fuse circuit and disconnect the address chip 58.

If all system components test out properly during the system test period, then timing of the analog to digital converter in accordance with the AC line frequency begins at 84 and the timing of any switching systems or multiplexors begins at 86. It is now possible to monitor the biopotential signals from a test area during a monitoring period begun at 88. During this monitoring period, conditions in the test area contacted by the electrode array 22 are stabilized so that subsequent reliable measurements of DC biopotentials can be obtained. Since the stabilization period for different subjects varies, some unknown time period must lapse before reliable measurements of DC biopotentials are obtained. Thus, at 88, a predetermined monitoring period is initiated, and the signals on all channels are monitored and averaged. Then, at the end of the initial monitoring period, the individual sample voltages are compared to the average of all voltages sampled during the measurement period to obtain a differential, and if the differential is greater than a predetermined value x, then sufficient signal stabilization has not occurred during the monitoring period and a new monitoring period is initiated. Conversely, if the differential signals are less than the predetermined value x, then the monitoring period is terminated and a test period is initiated.

With reference to FIG. 3, during the test period the digitized signals received from the various sequenced channels are monitored at 92 to determine whether or not each biopotential represented by the signals is within the range of from −30 to +100 millivolts. Digitized signals indicative of DC signals outside this range are discarded at 94 and the remaining signals are used to provide an average or normalized value for each channel at 96. The averaged value for each channel is obtained by summing the values obtained for that channel during the test period and dividing the sum by the number of measurements taken. Then, at 98, the central processor unit determines whether the test period has expired and the desired number of measurements have been taken, and if not, the collection of measurement samples or values continues.

Once the measurement or test period has expired, a final average value for each channel derived from the measurements taken during the span of the test period is available, and from these average values, the highest and lowest average value obtain during the test period is sampled at 100. The lowest average channel value is subtracted from the highest average channel value at 102 to obtain a maximum voltage differential value. This maximum voltage differential value is then processed at 104 to indicate the presence or absence of a disease, injury, or other bodily condition, and during processing, can be compared with previously obtained differential values to determine the efficacy of treatment or the progress of a disease, injury or other bodily condition. The differential value may also be used to indicate the occurrence of a number of normal bodily functions such as ovulation, and normal or abnormal labor conditions. In addition, for pattern recognition purposes, the digital signals stored by the central control unit and the average signals for each channel can be processed at 104 in a manner to be described.

A major design consideration for an effective DC biopotential measurement device 10 is to make the input impedance many times higher than that produced by the skin and sensor interfaces. Failure to do so results in decreased signal amplitude and, most important, loss of low frequency (e.g., DC) information. Sampling of DC potentials (e.g., number of samples and over what time period) ideally should be under computer control and it is here that microprocessor technology is utilized to its fullest. In digital systems, selection of the optimal sampling regimen is a balance between two factors:

1) acquiring enough samples per unit time to be representative of depolarization due to increased proliferation and 2) avoidance of taking samples over an extended time frame which might reflect DC drift. In other words, measuring the precise time slice of DC activity representative of cell proliferation is an important design consideration. It can be shown that reducing the number of DC samples per unit time can lead to irreproducible DC measurements.

Computer control of signal acquisition allows each electrode to be sampled via a multiplexed system. In a multiplexed system, each electrode output voltage is sampled multiple times in precise sequence, using a single amplifier or filter amplifier. Because only one amplifier (rather than multiple) amplifiers is used, this system ensures that individual channels are calibrated to each other. The resultant individual voltages are then averaged to provide a composite voltage for each electrode site. Since all individual samples can be stored and processed digitally, averaged voltages and variability in voltages over time can be analyzed for signal integrity. Comparisons of the averaged voltages are then used to identify areas of relative depolarization on the breast surfaces.

The fastest multiplexed DC measurement system currently available for breast electropotential evaluation can scan up to 96 electrodes 150 times over a 1.5 minute period. The array of sensors used in previous diagnostic studies consists of 16 measuring electrodes, which can be scanned 150 times each in about 18 seconds.

Pattern recognition of DC potentials is enhanced by effective filtering of the periodic electrical signals produced by cardiac and neural activity. These periodic signals typically range from about 1 Hz for cardiac signals to as much as 10 kHz for some neural signals. State-of-the-art digital filters are effective in keeping bandpass below 1 Hz. After filtering and averaging, DC voltages can be stored on tape or disk, displayed on a CRT, or printed. Typically, averaged voltages corresponding to each electrode are displayed, along with two measures of variability. These two measures are the Modified Range (MRNG) and test Reliability (REL). These measures can provide important information regarding signal voltage samples. It is a modified range because CPU programming sets a limit of 20 mV (i.e., +/−10 mV from the averaged voltage). If MRNG exceeds 20 mV, the individual voltages which exceed this value are filtered out and MRNG is recalculated. REL is expressed as a percentage of the 150 individual voltages and indicates how many individual voltages required filtering. High MRNG and low REL values may indicate that signal integrity has been compromised, perhaps by an electrode which has become disconnected from the patient.

One additional advantage of multiple electrode arrays is the richness of the data base which results from each patient test. As opposed to many other quantitative diagnostic and screening tests, such as serum assays, surface potential arrays provide multidimensional data. The key to effective diagnosis then becomes pattern recognition, which has become a science unto itself with the advent of sophisticated pattern recognition computer programs. Because concurrent measurements are made from a multiplicity of sites, surface potential analysis provides information across several dimensions. Differentials can be calculated from the entire breast or specific regions within the breast. Potential differences also can be compared between the two breasts (the between breast differential), or between corresponding pairs of sensors (mirror site differential). This wealth of quantitative information presents both an opportunity and a challenge to the goal of extracting signal patterns from an inherently noisy biological environment.

One approach to this kind of pattern recognition problem is to employ linear discriminant analysis. This can be effective in establishing a set of parameters which predict a given state, such as malignant vs benign disease. Its predictive value decreases if there are thresholds in the data. If thresholds in the data do exist, then nonlinear discriminant methods are called for. One recently developed approach is tree analysis, such as CART (Breiman et al. 1984), PIMPLE (Breiman, 1991), MARS, (Friedman, 1991), and SUPPORT (Chaudhuri, 1994). Decision trees, such as those produced by CART (Classification and Regression Trees) lead to a binary outcome (e.g., cancer vs benign states). Each decision point in the tree is referred to as a node in which optimal cut-off values are established based on variables considered for the study. CART arrives at the best decision tree for a data set first by constructing a very large tree using certain optimal criteria, and then pruning back the branches to reveal the key predictive variables. CART trees can be constructed with two parameters which can be controlled by the user. One parameter is tree complexity, which is used to penalize a non-significant large tree, which may not be predictive of future data sets. The other parameter is the cost ratio between false negative and false positive results, which in essence allows the user to determine the trade-off between test sensitivity and specificity.

The ability to trade sensitivity against specificity is a powerful advantage of electropotential analysis. In certain situations, such as disease screening, a high sensitivity is desired and reduced specificity can be tolerated. In diagnostic situations, it may be desirable for the test characteristic to feature high specificity. The use of CART allows objective control over these parameters.

Another nonlinear method which has gained popularity recently is the use of neural networks. As opposed to decision trees, which function as a process flow from node to node, neural network nodes (referred to as neurons) are arranged in two or three parallel levels. Information from one level can feed back to influence decision points at other levels in the network until a complex path of decision is made which can discriminate between disease states.

Regardless of which pattern recognition strategy is adopted, assessing the predictiveness of the decision matrix for new populations is essential. The traditional approach has been to collect data for a subgroup of patients, develop the decision matrix, and then validate the matrix on a new group of patients. The former group is referred to as the training data set and the latter group is referred to as the test data set. The decision matrix developed for the training data set is cross-validated for the test data set. In this way cross validation provides an index of how well the test sample will predict for the population for which the test method was developed for. Unfortunately, this strategy wastes resources by requiring the study to be run twice. In most studies data is a precious resource, and it is advantageous to use the largest possible population for development of the decision matrix. Therefore, statisticians have developed many data resampling methods which utilize the same sample for decision matrix formation and validation. The first resampling techniques, referred to as the jackknife and resampling cross validation, have been studied for several years. A newer resampling method, called the bootstrap (Efron, 1979) has been one of the most intensively researched methods in statistics during the past 15 years. The method consists of treating the existing sample as the population. One uses a computer to draw many samples from the test population in order to measure the bias between the sample and the population. Resampling cross validation calls for reiteratively sampling random segments of the data to be used for decision matrix formation, with residual segments being used for validation. For example, a decision matrix is constructed on a 90% sample of the population and then validated on the remaining 10%. Next, a different 90% sample is chosen at random and validated on the remaining 10%. The process is done recursively for numerous 90/10 splits of the data set. The total error generated by all the recursive samplings of the data base can be used as a surrogate for traditional validation techniques.

Once a decision matrix for disease diagnosis has been validated, it is programmed into the software for the CPU 42. This allows the test result to occur in real time. For each patient test, output from the device is anticipated to include averaged potentials from each electrode (along with MRNG and REL data), as well as a probability estimate as to whether the breast electropotential readings indicate the existence of malignancy. The physician would then use this information within the context the patient's total medical profile, which includes results from other tests and medical history to determine case management.

The DC biopotential sensing electrodes 24, 26 and 30 are responsible for transmitting ionic current from the skin of a subject through an electroconductive medium contained in the electrode, such as a cream or gel, which forms a conductive bridge between the skin surface and an electrode sensor element. The sensor element transduces ionic conduction to metallic conduction, and the resultant signal is then relayed by a cable system from the output of the sensing electrode.

Ions from the skin surface are driven into the electroconductive medium by electromotive force, or the physical propensity of ionic concentrations to equilibrate. At the gel or cream and sensor interface, a charge gradient between ions in the gel or cream and the discharge of ions from the sensor is formed. This has been referred to as the electrical double layer and can be visualized as two parallel sheets of charge with opposite sign. Maintenance of a stable double layer is an integral part of keeping noise to a minimum in DC measurement systems.

Another source of potential noise is resistance in a circuit, often referred to as Johnson noise, named after its discoverer. Resistance in any circuit creates spurious wide band voltages which result from the random motion of charge carriers in the conductor. Johnson noise can be ameliorated by using low resistance sensing electrodes and limiting the bandwidth of the measuring apparatus. Failure to control Johnson noise limits the level of minimum signal which is detectable.

The optimal single-use sensing electrode for biologic DC measurement requires both low DC offset and low resistance. This has been accomplished in accordance with the present invention by designing a sensing electrode which utilizes the excellent conductive properties of a low viscosity, high electrolyte content gel or cream, along with only one metallic component, such as silver. Such a design circumvents the problem of a dissimilar metals reaction which can be exacerbated by use of low viscosity, high electrolyte content gels and creams. Under strict manufacturing controls, sensors of this type can be made with DC offsets less than 0.5 mV and with very low impedance characteristics.

To compensate for sodium chloride present on the skin of a patient, which tends to mask sensed DC biopotential signals, a DC biopotential sensing electrode has been designed which incorporates an electroconductive medium in the form of a gel or cream which has a chloride ion content within or higher than the range of chloride present in isotonic or hypertonic fluids. This chloride ion content includes a substantial amount of sodium chloride ions as well as an equal or greater amount of ion conducting chloride, such as potassium chloride ions as well as an amount of calcium chloride ions, and this chloride is combined in a cream or gel formed from 8% to 35% solids mixed with water. The water must be free of impurities, such as heavy metals, which interfere with the DC biopotential signal sensed by the sensing electrode, and preferably pharmaceutical grade water is used in the formation of the gel or cream. The gel or cream is formed to have a pH within a range of 5.2 to 6.5, and a total chloride content within a range of 6–15 grams per hundred grams with a preferred chloride content within a range of 8–12 grams per hundred grams of gel or cream. The conductivity of the gel or cream is within a range of from 22,000 to 120,000 micromhos; the micromho being the inverse of impedance indicated by the ohm.

The chloride ion content in the electroconductive medium of the present invention is much higher than that in conventional pregelled AC biopotential sensing electrodes, and this high chloride content will rapidly cause corrosion to occur in a conventional electrode rendering the electrode useless after a minimal shelf life period. The novel DC biopotential sensing electrode of the present invention indicated generally at 106 in FIGS. 4 and 5, has been uniquely designed to have a long shelf life in spite of the high chloride content of the electroconductive medium used in the electrode and to exhibit both a low DC offset and a low AC impedance.

With reference to FIGS. 4–7, the DC biopotential sensing electrode 106 of the present invention includes a sensor element 108 having a sensor body 110. The sensor body is formed from a round sensor disc 112 and a mounting pin 114 which projects outwardly from the sensor disc. A first, lower surface 116 of the sensor disc provides an interface surface for contact with the electroconductive medium contained in the electrode, while a second opposed surface 118 from which the mounting pin projects provides a sealing surface for sealing the electroconductive medium within the electrode. The diameter of the sensor disc can affect the DC biopotentials sensed, and preferably the diameter is within a range of 0.39–0.43 inches.

The biopotential sensing electrode 106 includes only a single metal component which is highly resistant to corrosion when subjected to the high chloride content of the electroconductive medium for the electrode, for the inclusion of more than one metal would result in a bimetallic action that would enhance corrosion caused by chloride. Consequently, the body 110 of the sensor element 108 is formed of a nonmetallic material 120, such as plastic, glass, or a combination of both, and is then coated uniformly with a very thin coating 122 of an electrically conductive metal. The metal coating 122 is preferably only 1 mil. in thickness and should have a thickness within a range of 0.5 to 1.5 mil. If the coating is thinner, it becomes too thin to provide an even coating and to achieve equilibrium with the electroconductive medium, and if the coating is thicker, electrical resistance is increased to an undesirable level.

The metal coating 122 must evenly coat all surfaces of the nonmetallic material 120 and provide an unbroken layer of substantially uniform thickness. This coating may consist of an electrically or chemically deposited silver coating which is then electrically or chemically treated to form an outer film 124 of silver chloride and an inner layer 126 of silver.

Since the silver-silver chloride layer 122 is only 0.5 to 1.5 mil. in thickness, it could be scratched or chipped during electrode assembly, thereby interrupting the electrical conductive paths formed by this coating. To prevent such interruption, the sensing electrode 106 is provided with dual conductive paths so that a second electrical path is formed through the nonmetallic material 120. This is accomplished by using an electrically conductive nonmetallic material such as an electrically conductive plastic, glass, or glass-plastic combination. For example, a plastic such as ABS plastic, a glass, or a glass-plastic combination, impregnated with carbon within a total content range of from 20–40% by volume or weight has been found to be effective, and a preferred carbon content is 30% carbon by volume or weight.

The sensor element 108 is designed to engage an electrode terminal 128 and to transfer a DC signal thereto. This electrode terminal includes a terminal body 130 having a button connector section 132 projecting outwardly from an annular skirt 134. The button section is round in cross section, and the uppermost portion 136 thereof has a diameter of 0.151 inches or greater and is of a greater cross sectional diameter than the remainder of the button section. As will be noted from FIG. 6, the wall of the upper portion of the button section is of a greater thickness than the wall of the remainder of the button section.

The body 130 of the electrode terminal includes a central chamber 138 which is dimensioned to receive and tightly grip the mounting pin 114 of the sensor element 108. The edge of the opening into this central chamber is radiused at 140 to prevent surface chipping of the mounting pin as it enters and is forced into the central chamber. Additionally, the edge at the chamber innermost end is radiused at 141 to minimize cracking or chipping of the mounting pin 114 during assembly. The lead and trailing edges of the mounting pin are also radiused as indicated at 123 and 125, respectively. The radiused edges 123 and 141 are formed to conform and are thus radiused the same, while the edges 125 and 140 are also radiused equally but at a greater radius to form a larger arc than is formed at the edges 123 and 141. This provides a wider opening to the chamber 138.

It is important that the outer diameter of the mounting pin 114 conform to the inner diameter of the central chamber 138 within a close tolerance. Thus, with a chamber and pin diameter of 0.086 inches, these diameters should be formed to a tolerance of + or minus 0.001 inches.

Like the sensor element 108, the body 130 of the electrode 128 is formed of a nonmetallic material 142, such as plastic, glass or a combination of both coated uniformly with a thin coating 144 of electrically conductive metal. The metal coating on the nonmetallic material 142 must be formed of the same metal used to coat the nonmetallic material 120 of the sensor body 110 to preclude bimetallic support of corrosion within the biopotential sensing electrode 106. Also the thickness of metal coating 144 is preferably 1 mil. but is within a range of from 0.5 to 1.5 mil. When silver is used for the sensor element 108, silver will also be used to coat the electrode terminal 128. Preferably, a second electrical path is formed via the nonmetallic material 142 by using conductive plastic, glass or combination of both for this material. This plastic, glass or glass-plastic combination may be impregnated with carbon and has a carbon content which is preferably 30% but within a range of from 20 to 40% by volume or weight.

To insure that a uniform metal layer is formed on the sensor element body 110 and the electrode body 130, the outer edges 111 and 131, respectively, thereof are not substantially crowned but are radiused so that the metal layer is deposited evenly around each edge. Unradiused edges which provide a sharp edge or corner do not receive a uniform metal layer during electrical or chemical deposition and the metal layer on sharp edges is easily cracked or chipped. By providing relatively thick, radiused edges, the metal flows evenly around the edge during deposition and a uniform metal layer is achieved.

In the formation of the biopotential sensing electrode 106, a sheet of flexible, nonmetallic, liquid impervious barrier material 146 is positioned between the sensor element 108 and the electrode terminal 128 to form a barrier against the passage of liquid. This barrier material has a central opening 148 which permits the mounting pin 114 to pass through the barrier sheet and into the chamber 138 of the electrode terminal. The barrier sheet is adhered and sealed to the second surface 118 of the sensor disc 112 and with the sensor disc forms a primary seal to preclude passage of the electroconductive medium to the electrode terminal 128. When the mounting pin 114 is forced into the chamber 138, the bottom surface of the annular skirt 134 of the electrode terminal is forced into tight contact with the barrier sheet to compress this sheet between the annular skirt and the sensor disc thereby creating a secondary seal between the barrier sheet and the annular skirt. The barrier sheet is preferably formed of a foil material such as polyvinyl chloride.

A circular ring of flexible material 150 is secured and sealed to the barrier sheet 146 and is thicker than the barrier sheet so that a central opening 152 extending therebetween forms a well 154 which contains the electroconductive medium for the DC biopotential sensing electrode 106. The well is positioned relative to the barrier sheet so that the sensor disc 112 is centrally positioned in the well at the end thereof sealed by the barrier sheet. The diameter of the well defines the cross sectional area of a patient's skin which will be contacted by the electroconductive medium, and it should be within a range which is equal to the diameter of the sensor disc to one and one half times the diameter of the sensor disc. To insure that the sensor discs of adjacent electrodes are properly spaced, the outside diameter of the circular ring of flexible material 150 is at least three times the diameter of the sensor disc 112. Thus, if two biopotential sensing electrodes 106 are placed side by side with the edges of the circular rings of flexible material 150 in contact, the distance between the edges of the sensor discs of the two electrodes will be at least twice the diameter of the sensor discs, which is a minimum spacing between discs. If the biopotential sensing electrodes are to provide signals from which a differential value is derived, the sensor discs should be sufficiently spaced so that two adjacent electrodes are not sensing a DC biopotential from the same area of tissue.

The circular ring of flexible material 150 is preferably formed from a flexible foam, such as a cross-linked polyethylene foam, and includes a skin contact surface 156 which is coated with an adhesive acceptable for skin contact. It is this adhesive coated surface which adheres the biopotential sensing electrode 106 to the skin of a subject.

To limit the flow of electroconductive medium 158 from the well 154 and to provide surface tension to maintain the electroconductive medium in contact with the sensor disc 12, a disc 160 of reticulated open cell plastic foam is mounted in the well and is impregnated with the electroconductive medium. This disc 160 extends outwardly from the well beyond the skin contact surface 156, and permits the spread of the electroconductive medium onto the skin of a subject when the biopotential sensing electrode 106 is pressed in place. The open cell plastic foam disc is preferably formed of open cell polyurethene or open cell polyester foam with a cell count which is determined to some extent by the viscosity of the electroconductive medium. Generally the cell count for the plastic foam disc is within a range of from 35–45 cells per square inch.

In use, the disc 160 may be secured to the sheet of barrier material 146 or may be cut to a diameter slightly larger than the diameter of the well 154 so that it is retained in place within the well by tension.

Figure 8:
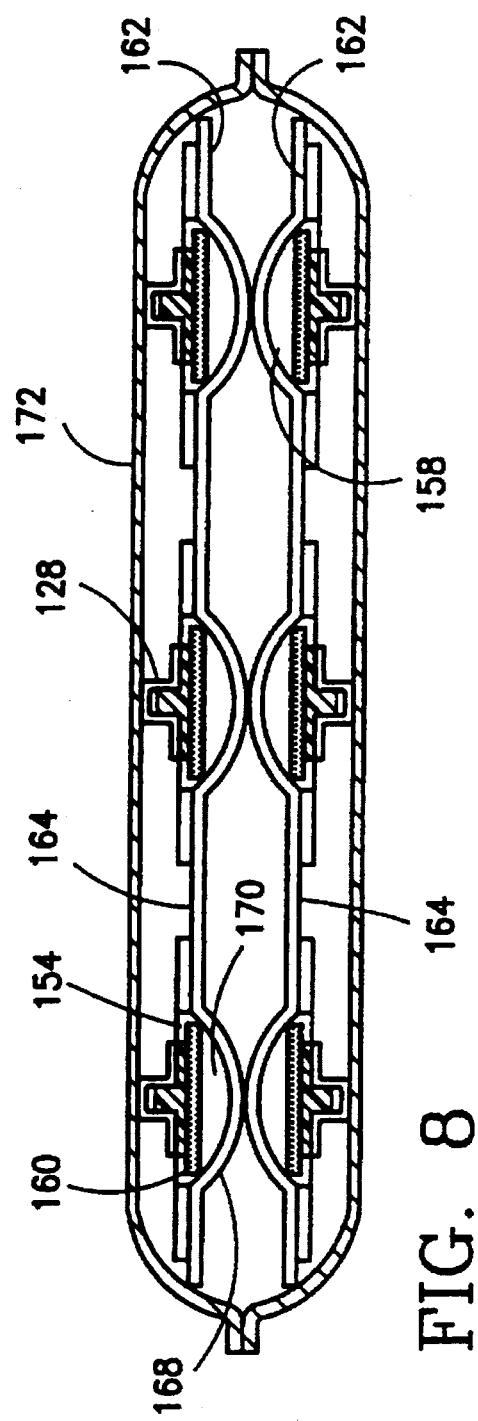
FIG. 8 is a cross sectional view of the packaging unit for the electrode of FIG. 4.
Figure 9:
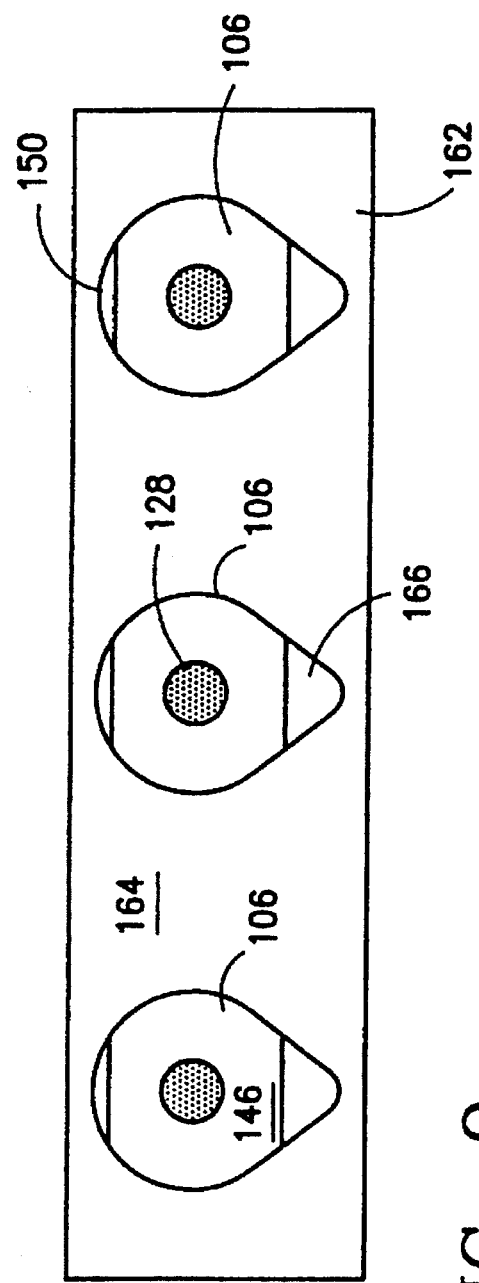
FIG. 9 is a plan view of the electrode of FIG. 4 and the adhesive release strip therefor.

The manner in which the DC biopotential sensing electrodes 106 of the present invention are packaged is quite important, for the high chloride ion content of the electroconductive material 158 causes the water in this material to evaporate rapidly if the electrodes are not properly packaged. Referring now to FIGS. 8 and 9, each electrode 106 is mounted upon a release liner 162 having an upper surface 164 which is an adhesive release surface. The skin contact surface 156 of the electrode 106 is adhered to this adhesive release surface by the adhesive acceptable for skin contact which coats this skin contact surface. To aid in removal of the electrode from the release surface of the release liner 162, the circular ring of flexible material 150 may be provided with a tab section 166, and the skin contact surface of this tab section is not coated with adhesive.

The release liner 162 is formed with a concave depression 168 extending outwardly from the release surface 164 thereof, and this concave depression forms a cavity 170 which opens at the adhesive release surface of the release liner. The diameter of this opening is substantially the same as the diameter of the well 154, and the release liner is positioned so that the well and the opening to the cavity 170 are substantially in alignment. Thus, the cavity 170 contains both the disc 160 of reticulated open cell plastic foam as well as the electroconductive medium which impregnates this disc. The release liner is formed of plastic or of similar fluid and air impervious material, and therefore, seals the electroconductive medium within the well 154 and the cavity 170. The release liner allows the reticulated foam to retain 95% or more of the electroconductive medium and provides a barrier which prevents dehydration of the electroconductive medium while allowing easy removal of the sensor from the release liner. To enable a user to insure that the electroconductive medium has not dried up or leaked away during storage of an electrode 106, the release liner is formed of a clear or transparent material, at least in the area of the concave depression 168, so that the electroconductive material in the cavity 170 and the well 154 may be observed. If visual observation indicates that there is not a sufficient amount of electroconductive material in the cavity 170 and the well 154, the electrode 106 should not be used.

As illustrated in FIGS. 8 and 9, the release liner 162 is preferably formed in strips with a plurality of electrodes 106 mounted upon each strip. To effectively package these electrodes in a manner which insures a long shelf life, two strips of electrodes are placed back-to-back with the concave depressions 168 thereof in contact and with the electrode terminals 128 facing outwardly. It is important that the electrodes be packaged so that the electrode terminals for electrodes in the package are prevented from contacting the electrode terminal of another electrode. The two strips of electrodes are then encased and sealed within a liquid, vapor and gas impervious outer package 172 which is preferably formed of metal foil. The combination of the metal foil outer package and the sealing action provided by the release liner effectively prevents evaporation of the liquid in the electroconductive medium 158.

For some DC biopotential measuring applications, it becomes desirable to be able to apply a plurality of electrodes substantially simultaneously and be assured that the electrodes are properly spaced for the measurement to be taken. This can be particularly advantages for breast screening applications where a large number of electrodes are sometimes used. Attempts have been made to use brassiere type structures to support the electrodes in a proper spaced relationship, but a brassiere is designed to slide over the breast, and this sliding contact results in removal of the electroconductive material from the electrodes mounted on the brassiere. Gel or cream loss results in improper screening results and poor adhesion of the electrodes. More importantly, however, is the fact that the sizing method currently used in conventional brassiere design is inadequate to permit the use of conventional brassieres as supports for breast sensing electrodes. Female breast sizes and volumes within a single brassiere size and cup value have been found to vary significantly. It has even been found that there are significant variations in size between the left and right breasts of single individuals. Consequently, brassiere type electrode supports of conventional size will not ensure that the electrode to breast contact required for accurate DC biopotential screening will be maintained.

Although there is a direct correlation between breast volume and breast anthropomorphic measurements, it has been found that the measurements should actually determine the sizing and layout of a biopotential breast screening array fixed to a supporting structure. Then, prior to the screening process, measurements of a subject can be taken and a properly sized electrode array chosen. Array sizing would be based upon three measurements; Z-N (lateral breast crease to nipple crease), A-N (axilla to nipple), and F-N (inframammary fold to nipple). Due to the broad range of existing breast measurements, an overlapping range for each measurement within at least the following five sizes has been found to be necessary.

| SIZE | Z-N (cm) | A-N (cm) | F-N (cm) |
|---|---|---|---|
| 1 | less than 0.7 | less than 12.4 | less than 7.5 |
| 2 | 8.0–10.5 | 12.0–15.0 | 6.0–8.4 |
| 3 | 9.7–12.5 | 13.5–16.0 | 7.9–9.5 |
| 4 | 11.5–14.0 | 15.0–16.0 | 9.0–12.0 |
| 5 | 13.0 and greater | 17.0 and greater | 10.5 and greater |

Figure 10:
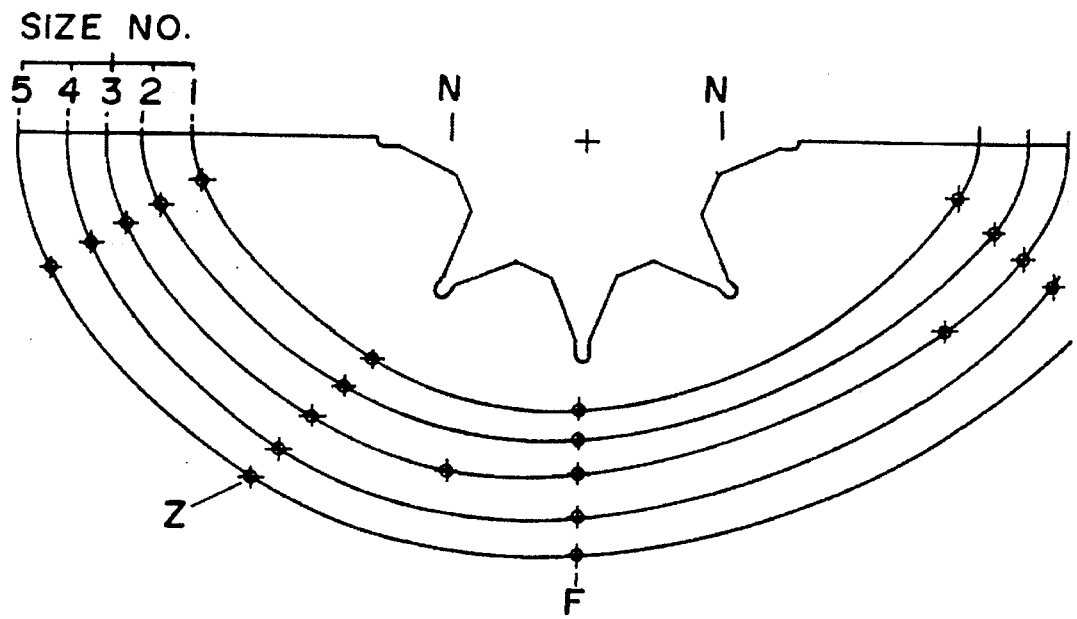
FIG. 10 is a diagram illustrating the sizing and electrode placement for a breast-screening electrode array.

To determine which size of apparatus to use during the screening of a patient, the suggested measurements are taken and then the smallest appropriate size is selected with ranges in which all three measurements fall. By using this sizing method, electrode supports for breast screening can be formed to one of the five indicated sizes with electrode placement as illustrated by the chart of FIG. 10.

A properly positioned screening array of sensor electrodes would allow mapping of potentials of points in between the sensors by using vector interpolation. Thus a graphic representation of surface electrical potential of all points or areas on the breast surfaces could be accomplished. Color coding (or grey scale) corresponding to various levels of potential would provide visual imaging of the surface potential maps of both breasts. Vector interpolation involves summing the point source measurements (that is, the potential measurements actually measured from the skin surface) for each unmeasured point on the breast as a function of the distance each point source measurement is from the interpolated area. Various interpolation models could be used which would take into account curvature and size of the breast, and number of point sources measured.

Figure 11:
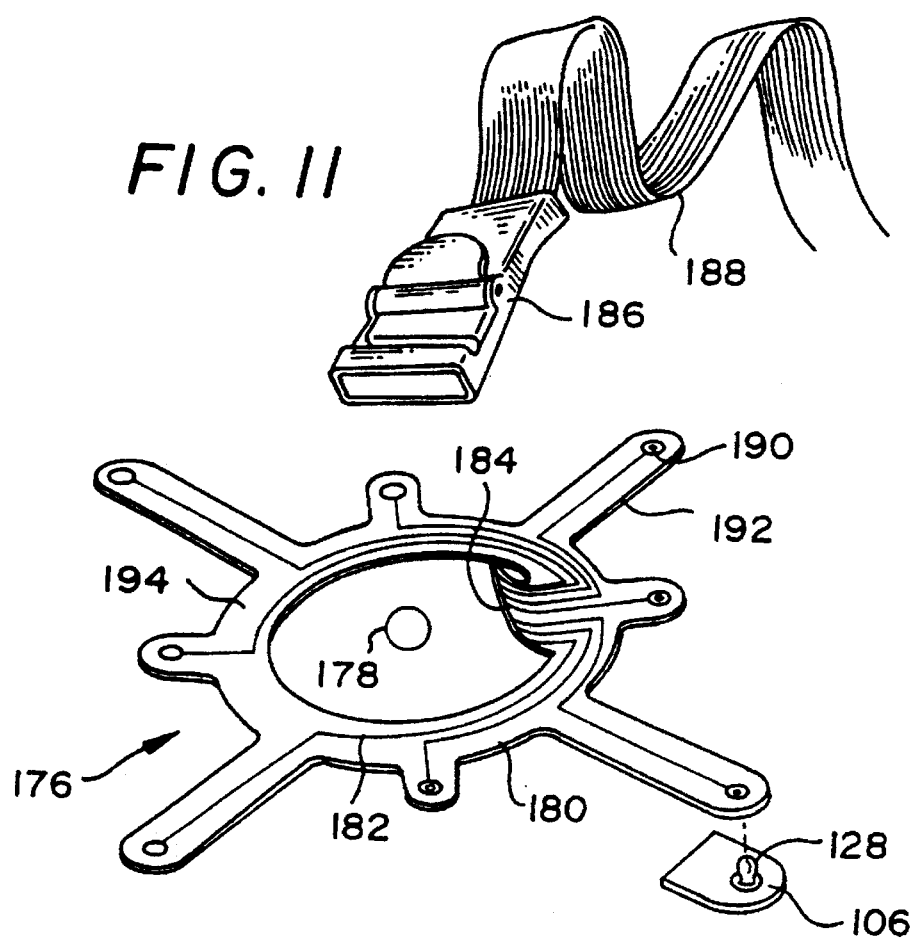
FIG. 11 is an exploded perspective view of a lattice electrode array of the present invention.

To satisfy the sizing criteria necessary for effective breast screening, lattice type electrode arrays and wrap around electrode arrays have been developed to form at least a portion of the electrode array 22 of FIG. 1. Referring to FIG. 11, a simple lattice array 176 is illustrated which operates effectively as an aid in assuring proper electrode placement on a breast to be screened. The array is designed to be placed on the breast with the nipple 178 as the center registration point for the array, and the array is sized to one of the five sizes dependent upon measurements to the nipple as previously described. The basic lattice support 180 for the array is formed from thin, flexible, lightweight electrical insulating material, such as 10 MIL clear polyester film, which has been cut to the desired shape. The electrical circuitry 182 leading to each electrode for the array 176 is printed on the lattice support 180 with conductive ink or other printed circuit material, and the individual circuits extend in spaced relationship to one or more attachment tabs 184 formed from the polyester film. These individual circuits are connected to the apparatus 10 by a ribbon cable connector 186 which snaps onto the attachment tab 184 to connect each individual electrode printed circuit to a ribbon cable 188 which includes a separate lead for each electrode circuit. The lattice support has a conductive electrode mounting grommet 190 at the end of a radiating arm 192 of the lattice support, and a plurality of the radiating arms project outwardly from a central support ring 194. The electrode terminal 128 of an electrode 106 snaps into each of the electrically conductive mounting grommets 190, and each grommet is connected to a separate electrical circuit 182.

The lattice array 176 with the electrodes 106 in place can be positioned on a breast to be screened without sliding contact and the radiating arms 192 are easily curved to conform to the curved surface of the breast.

Referring to FIGS. 12 and 13, a lattice type electrode array 196 carrying many more electrodes than those shown for the array 176 of FIG. 11 can be formed using a thin mylar or polyester film as a flexible support for the electrodes. In complex lattice arrays of this type, the electrodes are formed directly on circular pads 198 formed on the various radiating arms of the film. As in the case of the lattice array 176, separate conductive paths 200 are formed on the film by conductive ink or other printed circuit techniques, and these circuit paths all terminate at attachment tabs 202 and 204 which are connected to the apparatus 10 by ribbon cable conductors and ribbon cables of the type shown at 186 and 188 in FIG. 11.

With reference to FIG. 13, the actual construction of each of the electrodes formed on the lattice array 196 is illustrated. On one side of the pad 198, the conductive path 200 is formed, and this conductive path includes a terminal contact 206 which is positioned over an aperture 208 in the pad 198. On the opposite side of the pad, a layer of liquid impervious barrier material 210 is adhered to the pad, and this layer of barrier material includes a central aperture 212 to receive the mounting pin 114 of the sensor element 108. This mounting pin extends through the aperture 212 and the aperture 208 and is an electrical contact with the terminal contact 206. The sensor disc 112 is adhesively sealed to the barrier material 210, and the barrier material is also sealed to a circular ring of flexible material 150 as previously described. The well 154 of the circular ring of flexible material 150 includes the disc 160 of reticulated open cell plastic foam, and this disc is impregnated with the electroconductive medium for the electrode. The well 154 is closed by a release liner 162 having the cavity 170 to retain the electroconductive medium and the reticulated foam 160. The release liner may be formed as a large single sheet which extends beneath the complete lattice array 196 and which includes a depression 168 and cavity 170 beneath each electrode in the lattice array. In use, the thin film of the lattice array may be easily curved to conform to the curved surface of a breast or other portion of a subject while maintaining relative positioning between the electrodes of the array.

An electrode assembly formed in accordance with the present invention may be packaged as an integral disposable unit as illustrated in FIG. 14. With reference to FIG. 14, the prepackaged disposable electrode array indicated generally at 214 includes a lattice electrode assembly 216 including five electrodes mounted upon a lattice film support 218. This lattice film support and the electrodes mounted thereon are similar to that shown in FIG. 11, with the exception that the lattice support does not include the conductive ink circuits shown in FIG. 11. Instead, the terminals 128 for the electrodes are engaged by snap terminals 220, each of which is connected to a separate conductor 222. The conductors 222 lead to an electrical connector 224 which may be plugged into the circuit to the low pass filter amplifier 36 of FIG. 1. The connector 224 also includes the address chip 58 and the conductor 54 to provide a connection to the conductor 56. Since the terminal snaps 220 could be removed and connected to other sensing electrodes not suited for use with the device 10 of FIG. 1, the address chip 58 is preferably combined with circuitry of the type previously described so that the address circuitry in the connector 224 is deactivated by the central processor 42 once the address circuitry has been interrogated and provided a proper address.

In addition to the lattice electrode array 216, separate individual electrodes 226 of the type shown in FIGS. 4 and 5 are also connected to the connector 224 by separate cables 222. The electrode lattice array 216 and the individual electrodes 226 as well as the cables 222 and the connector 224 are packaged in a disposable packaging unit 228 which includes a layer of shock absorbing material 230, such as plastic foam or a shock absorbing paper or cardboard layer. This shock absorbing material 230 is provided with cut away depressions 232 and 234 to receive the lattice array 216 and the electrodes 226, respectively, as well as a cut away channel 236 for the cables 222 leading to a cut away section 238 for the connector 224. The bottom wall of the cut away sections 232 and 234 is formed by a layer of adhesive release material 240 formed in the same manner as the release material 162 of FIGS. 8 and 9. The layer of release material 240 includes the cavities 170 positioned beneath the electrodes in the lattice array 216 as well as beneath each of the electrodes 226.

The lattice array 216 and separate cables 222 may be replaced by either of the lattice arrays 176 or 196 connected by the cable connectors 186 and ribbon cables 188 to the electrical connector 224.

Industrial Applicability

The DC biopotential sensing electrodes and electrode assemblies of the present invention may be effectively employed with an apparatus for screening or sensing disease states, injury sites or bodily conditions in a living organism by detecting the DC biopotential of the electromagnetic field present between a reference and a plurality of test points on the living organism. These electrodes and electrode assemblies provide an accurate measurement of the gradient of an electrical activity which occurs as a function of biological activity and yet are designed to resist corrosion and provide an extended shelf life.

We claim:

1. A biopotential sensing electrode for contact with a skin surface of a human or animal subject and suitable for sensing DC biopotentials comprising:

an electrode sensing element, an electrode terminal connected to said electrode sensing element to conduct an electrical potential therefrom, said electrode sensing element and electrode terminal each being formed from a nonmetallic, electrically conductive material to form a first electrically conductive path and coated with a uniform coating of silver having a thickness within a specified range of from 0.5 to 1.5 mil to form a second electrically conductive path, said nonmetallic electrically conductive material being formed of plastic, glass or a combination of both impregnated with carbon, said carbon being within a range of from 20 to 40% by weight of the nonmetallic conductive material, and an electroconductive medium for contact with the skin surface of a subject contacting said electrode sensing element for relaying a biopotential from the skin surface of a subject to said electrode sensing element.

2. A biopotential sensing electrode for contact with a skin surface of a human or animal subject and suitable for sensing DC biopotentials comprising:

an electrode sensing element having a sensor body including a round disc having first and second substantially parallel opposed surfaces, and a mounting pin projecting centrally from the second surface of said disc, said disc having a diameter within a range of from 0.39 to 0.43 inches, the sensor body of said electrode sensing element being formed from an electrically conductive plastic, glass or a glass-plastic combination completely and uniformly coated with an electrically conductive silver/silver chloride coating, said coating having a thickness within a range of from 0.5 to 1.5 mil, said plastic, glass, or glass-plastic combination being impregnated with carbon to form an electrically conductive plastic-carbon, glass-carbon or plastic/glass carbon combination to provide a conductive path independent of said silver/silver chloride coating, an electrode terminal connected to said electrode sensing element to conduct an electrical potential therefrom, said electrode sensing element and electrode terminal each being formed to include a first and a second electrically conductive path, and an electroconductive medium for contact with the skin surface of a subject contacting the first surface of said round disc of said sensor body for relaying a biopotential from the skin surface of a subject to said electrode sensing element.

3. A biopotential sensing electrode assembly comprising:

a thin, flexible support sheet of electrical insulating material, said support sheet including an opening and an annular section extending around said opening, a plurality of separate radially extending legs extending outwardly from said annular section, said radially extending legs providing a flexible support for one or more biopotential sensing electrodes, and biopotential sensing electrodes for contacting a subject mounted on said legs, each such biopotential sensing electrode including an electrode sensing element including a sensor body with a sensor disc having first and second opposed surfaces and a mounting pin projecting from the second surface of said disc, an electrode terminal connected to said electrode sensing element to conduct an electrical potential therefrom, a flexible plastic sheet of liquid impervious barrier material positioned between said electrode terminal and said electrode sensing element, said barrier material being adhered to the second surface of said sensor disc to form a liquid seal and including an aperture through which said mounting pin projects, a layer of flexible plastic material affixed to said sheet of barrier material, said layer of flexible plastic material having an aperture extending therethrough to form a well for receiving an electroconductive medium, the sensor disc of said electrode sensing element being positioned in said well, said sheet of barrier material extending outwardly from said sensor disc to close and seal a first end of said well, and an electroconductive medium for contacting a subject and transmitting a biopotential from the subject to said electrode sensing element, said electroconductive medium being received in said well in contact with the first surface of said sensor disc.

4. The biopotential sensing electrode assembly of claim 3 wherein said radially extending legs each include a first leg surface and a second leg surface parallel to and opposed to said first leg surface and at least one aperture extending through said flexible support sheet between said first and second leg surfaces, said electrode terminal is formed on the second leg surface of a radially extending leg and said sensing element mounting pin projects through said aperture from said first leg surface into contact with said electrode terminal.

5. A biopotential sensing electrode for contact with a skin surface of a human or animal subject and suitable for sensing DC biopotentials comprising:

an electrode sensing element formed from a nonmetallic, electrically conductive material forming a first electrode electrically conductive path, said nonmetallic electrically conductive material being entirely coated with a uniform external coating of an electrically conductive metal, said electrically conductive metal coating forming a second electrode electrically conductive path, an electrode terminal formed from a nonmetallic, electrically conductive material forming a first terminal electrically conductive path, said nonmetallic electrically conductive material forming said terminal being entirely coated with a uniform external coating of the same conductive metal which coats said electrode sensing element to form a second terminal electrically conductive path, said electrode terminal being connected to said electrode sensing element to conduct an electrical potential therefrom, the conductive metal coating for both said electrode sensing element and said electrode terminal being of a thickness within a range of from 0.5 to 1.5 mil, and an electroconductive medium for contact with the skin of a subject contacting said electrode sensing element for relaying a biopotential from the skin of a subject to said electrode sensing element.

6. The biopotential sensing electrode of claim 5 wherein said conductive metal is silver.

7. The biopotential sensing electrode of claim 6 wherein said silver coating is of a thickness of 1 mil.

8. The biopotential sensing electrode of claim 5 wherein said electrode sensing element includes a sensor body including a round disc having first and second, substantially parallel opposed surfaces, said first surface contacting said electroconductive medium and a mounting pin projecting centrally from the second surface of said disc.

9. The biopotential sensing electrode of claim 8 wherein said electrode terminal includes a terminal body having a button connector section having a first end and a second closed end, an annular skirt section extending outwardly from said first end of said button connector section, said terminal body having a chamber extending centrally of said button connector section from said second, closed end and opening at the first end, said chamber being dimensioned to receive and retain the mounting pin of said electrode sensing element, said button connector section having a round cross section, the cross section of the button connector section in a first area adjacent to said second end thereof being greater than the cross section of the button connector section in a second area including the rest of said button connector section, the cross section of said button connector section adjacent to said second end having a diameter of 0.151 inches or more.

10. The biopotential sensing electrode of claim 9 wherein the electrically conductive metal on said terminal body is a silver layer and the electrically conductive metal on said sensor body is formed by an inner layer of silver and an outer layer of silver chloride.

11. The biopotential sensing electrode of claim 10 wherein the said sensor and terminal bodies are formed of plastic, glass, or a glass-plastic combination, impregnated with a nonmetallic, electrically conductive material to form a second conductive path therethrough, said electrically conductive metal forming a first electrically conductive path.

12. The biopotential sensing electrode of claim 11 wherein said electrically conductive material is carbon, the carbon content of said carbon impregnated plastic, glass or glass-plastic combination being within a range of from 20–40% by weight.

13. The biopotential sensing electrode of claim 9 which includes a flexible sheet of a nonmetallic liquid impervious barrier material positioned between said electrode terminal and the second surface of the round disc of the sensor body of said electrode sensing element, said sheet of barrier material including an aperture through which said mounting pin projects to the chamber of said button section, the second surface of said round disc and the annular skirt section of said terminal body being engaged with said barrier material when said mounting pin is retained in said button section chamber.

14. The biopotential sensing electrode of claim 13 wherein a layer of flexible plastic material is affixed to said sheet of barrier material, said layer of flexible plastic material having a circular central aperture extending therethrough to form a well for receiving said electroconductive medium, the round disc of the sensor body of said electrode sensing element being centered in said circular central aperture, said sheet of barrier material extending outwardly from said round disc to close and seal a first end of said well.

15. The biopotential sensing electrode of claim 14 wherein said layer of flexible plastic material is substantially circular in configuration, said round disc of the sensor body of said electrode sensing element having a diameter within a range of from 0.39 to 0.43 inches, said layer of flexible plastic material having an outer diameter at least three times the diameter of said round disc.

16. The biopotential sensing electrode of claim 15 wherein said layer of flexible plastic material is a layer of plastic foam having a contact surface extending annularly of said well and spaced from the end of said well which is closed by said sheet of barrier material, said contact surface being coated with an adhesive acceptable for skin contact.

17. The biopotential sensing electrode of claim 16 wherein the diameter of said well is within a range of from a diameter equal to the diameter of the round disc of said sensor body to 1½ times the diameter of said round disc.

18. The biopotential sensing electrode of claim 17 wherein a layer of open cell reticulated plastic foam is mounted in said well in contact with the first surface of the round disc of the sensor body, said reticulated foam layer being impregnated with said electroconductive medium.

19. The biopotential sensing electrode of claim 18 wherein said reticulated foam layer covers the first surface of said round disc of the sensor body, said reticulated foam layer extending outwardly from said well beyond the contact surface of said layer of flexible plastic material.

20. The biopotential sensing electrode of claim 19 wherein said reticulated open cell foam layer has a cell count within a range of from 35–45 cells per square inch.

21. The biopotential sensing electrode of claim 19 which includes a release liner provided to receive and retain said reticulated open cell foam layer and said electroconductive medium, said release liner having a adhesive release surface adhered to the adhesive on the contact surface of said layer of plastic foam and being formed with a cavity extending outwardly from a surface of said release liner opposite to said release surface, said cavity opening at said release surface and being positioned over the well in said layer of plastic foam to receive said reticulated foam layer and said electroconductive medium.

22. The biopotential sensing electrode of claim 21 wherein said cavity is formed of transparent or clear material to permit inspection of the electroconductive medium contained in said well and cavity.

23. The biopotential sensing electrode of claim 22 wherein said cavity is substantially circular with a diameter which is substantially equal to the diameter of said well.

24. A DC biopotential sensing electrode for contact with a skin surface of a human or animal subject comprising:

an electrode sensing element, an electrode terminal connected to said electrode sensing element to conduct an electrical potential therefrom, said electrode sensing element and electrode terminal each being formed from a nonmetallic, electrically conductive material completely and uniformly coated with a metallic coating of the same noncorrosive metal, said metallic coating having a thickness within a range of from 0.5 to 1.5 mil, and constituting the only metallic component of said sensing electrode and an electroconductive medium for contact with the skin surface of said subject contacting said electrode sensing element for transmitting a biopotential from the skin surface to said electrode sensing element, said electroconductive medium having a chloride content within a range of from 6–15 grams per hundred grams of electroconductive medium.

25. The biopotential sensing electrode of claim 24 wherein said metallic coating is silver.

26. The biopotential electrode of claim 25 wherein the silver coating on said electrode sensing element includes a uniform layer of silver chloride over a layer of silver.

27. A biopotential sensing electrode for contact with a skin surface of a human or animal subject and suitable for sensing DC biopotentials comprising:

an electrode sensing element which includes a sensor body including a round disc having first and second substantially parallel opposed surfaces, and a mounting pin projecting centrally from the second surface of said disc, an electroconductive medium for contact with the skin surface of said human or animal subject contacting said electrode sensing element for relaying a biopotential from said skin surface of said human or animal subject to said electrode sensing element, said electroconductive medium contacting said first surface of said round disc, and an electrode terminal connected to said electrode sensing element to conduct an electrical potential therefrom, said electrode terminal including a terminal body having a button connector section with a first end, a second closed end, and an annular skirt section extending outwardly from said first end of said button connector section, said button connector section having a round cross section, the cross section of the button connector section in a first area adjacent to the second end thereof being greater than the cross section of the button connector section in a second area of said button connector section which includes all of said button connector section with the exception of said first area, the round cross section of said button connector section in said first area having a diameter of 0.151 inches or more, said terminal body having a chamber extending centrally of said button connector section from said second closed end and opening at said first end, said chamber being dimensioned to receive and retain the mounting pin of said electrode sensing element, said electrode sensing element and electrode terminal each including a first and a second electrically conductive path and each including only one metallic component formed of the same electrically conductive metal.

* * * * *